United States Patent [19]

Squires et al.

[11] Patent Number: 4,690,897

[45] Date of Patent: Sep. 1, 1987

[54] METHOD FOR TRANSFORMATION OF ANAEROBIC MICROORGANISMS

[75] Inventors: Charles H. Squires, Boulder; Donald L. Heefner, Arvada; Ronald J. Evans, Beatrice J. Kopp; Michael J. Yarus, Boulder, all of Colo.

[73] Assignee: Synergen Associates, Inc., Boulder, Colo.

[21] Appl. No.: 535,933

[22] Filed: Sep. 26, 1983

[51] Int. Cl.$^4$ .............. C12N 15/00; C12N 1/00; C12P 21/00; C12R 1/145
[52] U.S. Cl. ..................... 435/320; 435/68; 435/172.3; 435/842; 935/29; 935/56
[58] Field of Search .............. 435/68, 253, 172.3, 435/317, 826, 842; 935/14.29, 56, 60, 72-74

[56] References Cited

U.S. PATENT DOCUMENTS 4,332,900 6/1982 Manis et al. ................ 435/172.3
4,477,576 10/1984 Chang et al. ................ 435/253
4,493,893 1/1985 Mielenz et al. .............. 435/172.3

FOREIGN PATENT DOCUMENTS 0063764 11/1983 European Pat. Off. ......... 435/172.3

OTHER PUBLICATIONS

Allcock et al, *App and Env Micro*, vol. 43(3) pp. 719-721, Mar. 1982, "Clostricium Acetobutylicum Protoplast Formation and Regeneration".
Rood et al, *Plasmid*, vol. 1, pp. 563-570, 1978, "Identification of a Transferable Tretracycline Resistance Plasmid CW3 from *Clostridium Perfringens*".
Madoff, Subrelle *The Prokcyotes*, Springer-Verlag, vol. VII pp. 2225-2236, 1981.

*Primary Examiner*—Thomas G. Wiseman
*Assistant Examiner*—Robin Lyn Teskin
*Attorney, Agent, or Firm*—Finnegan, Henderson, Farabow, Garrett & Dunner

[57] ABSTRACT

Method for transforming anaerobic microorganisms. Anaerobic microorganisms are induced to form L-forms. Genetic material capable of inducing the desired phenotype is introduced into the L-forms, after which the L-forms may be caused to regenerate their cell wall. These methods are also useful for obtaining desired biological products. Additionally, shuttle vectors capable of transforming both aerobic and anaerobic microorganisms are set forth.

8 Claims, 3 Drawing Figures

METHOD FOR TRANSFORMATION OF ANAEROBIC MICROORGANISMS

BACKGROUND OF THE INVENTION

The present invention relates to a method for transformation of anaerobic microorganisms and constructing shuttle vectors useful in the transformation. Specifically, the present invention relates to a method for transformation of bacteria belonging to the genus Clostridium W1 and to a family of shuttle vectors capable of transforming both anaerobic and aerobic species, such as species of Clostridium W1 and *Escherichia coli* (*E. coli*).

Anaerobic microorganisms are capable of growth in an environment lacking oxygen. Anaerobic microorganisms are usable in large-scale fermenters, where the ability to reproduce and to produce biological products in an environment lacking oxygen is perceived as an advantage. One reason that the ability to exhibit anaerobic growth is an advantage is that costly aeration apparatus for the fermentation vats need not exist when anaerobic organisms are grown in the vats. In addition, certain fermentation procedures exist where aeration is impossible. In these situations, it is necessary that an anaerobic microorganism be capable of carrying out the desired fermentation. Secondly, the possibility of contamination with aerobes is eliminated when an anaerobic environment is used. Thirdly, several anaerobic species are of special interest, both medically and commercially, for their abilities to produce toxins, use cellulose or pentoses as substrates, fix nitrogen, and produce useful bulk chemicals, such as acetone, butanol, acetic acid and ethanol as end products. For these reasons, methods have been sought which can be used to endow anaerobic microorganisms with additional genetic capabilities to produce novel biological products.

A method for endowing anaerobic microorganisms with the ability to produce useful biological products would be to transform the microorganism with plasmid DNA containing foreign genetic material, including genetic material from aerobic organisms, capable of directing the microorganism to produce the desired biological product. However, the inventors are unaware of any successful prior art transformation attempts that have resulted in a useful gene transfer system for anaerobic microorganisms. In fact, unsuccessful attempts at such a transformation using anaerobic microorganisms, such as that noted in Reid, S. J., E. R. Allcock, D. T. Jones, P. R. Woods, 1983, App. and Environmental Micro. 45: 305–307, have been published. In response to the commercial need for a method for transformation of anaerobic microorganisms, and in spite of previously reported unsuccessful attempts, the inventors have developed a method for transformation particularly applicable to anaerobic microorganisms more fully described below.

SUMMARY OF THE INVENTION

The present invention overcomes the problems and disadvantages of the prior art by setting forth a method for transformation of anaerobic microorganisms which includes the production of so-called "L-forms". L-forms are microorganisms from which the cell wall has been removed by one or a combination of techniques outlined below. Following removal of the cell wall, these organisms are capable of cell division and therefore growth, provided they are maintained in a medium which prevents excessive movement of water through the cell membrane. In the preferred embodiment, the L-forms are regenerated after transformation into viable microorganisms having cell walls. The present invention also provides novel shuttle vectors for the transformation of both aerobic and anaerobic bacteria, particularly anaerobic bacteria of the genus Clostridium and aerobic bacteria of the genus Escherichia. Moreover, the present invention overcomes the problems of the prior art by providing the means by which novel biological products may be produced in an anaerobic environment.

Additional objects and advantages of the invention will be set forth in part in the description which follows, and in part will be obvious from the description or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, a method for transformation of anaerobic microorganisms according to the present invention comprises the steps of (a) inducing anaerobic microorganisms to form L-forms; (b) introducing into the L-form foreign genetic material capable of inducing the microorganism to exhibit a desired phenotype; and (c) if desired, causing the L-forms to regenerate cell walls.

Further, to achieve the foregoing objects and in acccrdance with the purpose of the invention, as embodied and broadly described herein, a method for producing biological products in an anaerobic environment according to the present invention comprises the steps of (a) inducing anaerobic microorganisms to form L-forms; (b) introducing into the L-forms foreign genetic material capable of causing the microorganisms to produce the desired biological product; (c) if desired, causing the L-forms to regenerate cell walls; (d) selecting those microorganisms, with regenerated cell walls if desired, capable of producing the desired biological product and (e) producing that product anaerobically using such microorganisms.

Still further to achieve the foregoing objects and in accordance with the purpose of the invention, as embodied and broadly described herein, shuttle vectors are set forth which comprise genetic material capable of being inserted into both an L-form of an anaerobic microorganism and into an aerobic microorganism to cause both the anaerobic microorganism and the aerobic microorganism to exhibit a desired phenotype.

The accompanying drawings, which are incorporated in and constitute a part of this specification, illustrate embodiments of the invention and, together with the description, serve to explain the principles of the invention.

Plasmid pCP1, which is a chimeric plasmid comprised of *E. coli* plasmid pBR322 and *Clostridium perfringens* plasmid p28a.

Plasmid pCP7, which is a plasmid used in the transformation of *E. coli* and which serves as a precursor for shuttle vectors pCP12 and pCP13.

Plasmid pCP10, which is a plasmid used in the transformation of *E. coli* and which serves as a precursor for shuttle vector pCP16.

Figure 3:
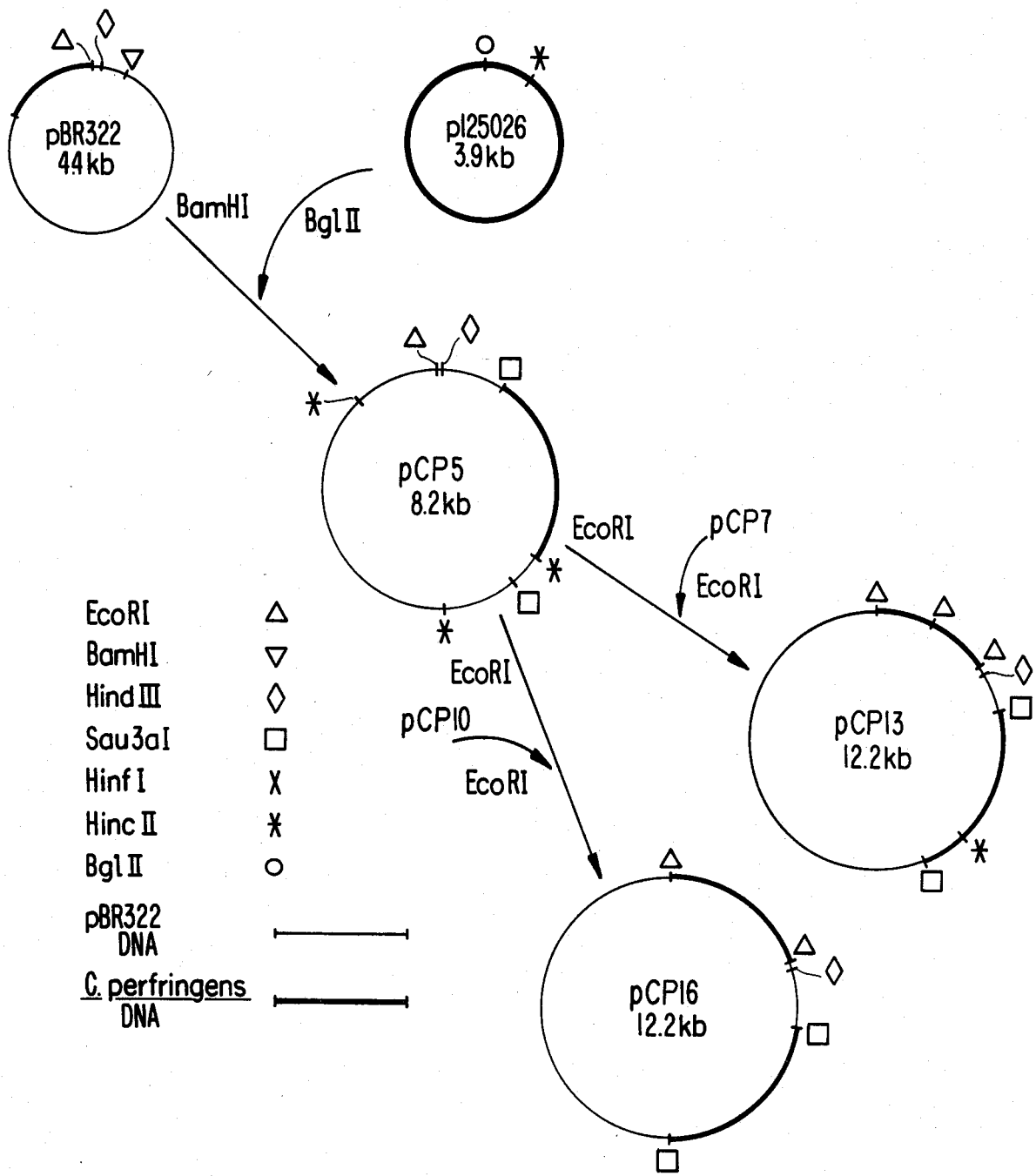

FIG. 3 illustrates the genealogy and the restriction maps of the following plasmids:

Plasmid pCP5, which is a chimeric plasmid comprised of *E. coli* plasmid pBR322 and *C. perfringens* plasmid p12502b and which serves as a precursor for shuttle vectors pCP13 and pCP16.

Plasmid pCP13, which is a shuttle vector used in the transformation of *E. coli* and *Clostridium perfringens*.

Plasmid pCP16, which is a shuttle vector used in the transformation of *E. coli* and *Clostridium perfringens*.

DETAILED DESCRIPTION OF THE PREFERRED EMBODIMENT

Reference will now be made in detail to the presently preferred embodiments of the invention, examples of which are illustrated in the accompanying drawings.

Transformation Method

In accordance with the invention, a method for transformation of an anaerobic microorganism comprises (a) inducing the anaerobic microorganisms to form L-forms; (b) introducing into the L-forms foreign genetic material capable of causing the microorganisms to express a desired phenotype; and, in the preferred embodiment and if desired, (c) causing the L-forms to regenerate cell walls.

The method of the present invention is useful for the transformation of anaerobic microorganisms. As used hereinafter, the term anaerobic microorganism is intended to include both obligate anaerobic and facultative anaerobic microorganisms. Particularly, the method of the present invention is useful for the transformation of gram-positive, spore-forming anaerobic bacteria. More specifically, the method of the present invention is useful for the transformation of bacteria of the family Bacillaceae, particularly those bacteria of the genus Clostridium, and especially *Clostridium perfringens* (hereinafter referred to as *C. perfringens*). It is contemplated that the method of the present invention may also be applied to the transformation of other species of Clostridium, including *Clostridium acetobutylicum* and *Clostridium pasteurianum*.

To transform an anaerobic microorganism, it is necessary that the microorganism be induced to form an "L-form," that is, be denuded of its cell wall. Any method known in the prior art or hereafter discovered capable of yielding a viable organism without a cell wall but still capable of regenerating its cell wall under appropriate conditions may be used in accordance with the present invention. Methods of obtaining microorganisms capable of growth without cell walls contemplated for use herein include, but are not limited to, growing the microorganisms in the presence of a substance which inhibits cell wall formation; reversible destruction of the cell wall of the organism with an appropriate enzyme, such as lysozyme; exposing the microorganism to a selective environment which causes spontaneous formation of wall-less organisms, or the like. Hereinafter, L-forms formed by a spontaneous selection process will be referred to as "autoplasts".

L-forms are created, in one embodiment of the present invention, by growing anaerobic microorganisms in the presence of a substance capable of inhibiting cell-wall formation. A substance capable of inhibiting cell-wall formation is one which biochemically interferes with cellular processes that form precursors to the cell wall or that form the cell wall itself. Such inhibiting substances include, but are not limited to, antibiotics such as penicillin, particularly Penicillin G, and ampicillin.

For example, L-forms to be used in transformations may also be obtained in the following way. Whole cells of *C. perfringens* are streaked onto a petri plate containing an osmotically stabilizing enriched medium containing an antibiotic. Preferably, such antibiotic is Penicillin G and is preferably present in a concentration of about 15 μg/ml. After overnight incubation, preferably at 37° C, quantitative appearance of L-form colonies is observed. If one of these colonies is then transferred to osmotically protective liquid medium not containing the antibiotic and incubated, the L-forms begin to divide after a lag of about 2–3 days and form a turbid culture within about 4 days. Further subculturing into the same medium results in growth with no lag and a doubling time of approximately 40 minutes.

This technique is particularly useful for the formation and transformation of anaerobic L-forms which are to remain as L-forms after transformation, since it may be difficult to regenerate the cell wall of the transformed L-form. Although somewhat more delicate than transformed anaerobes with regenerated cell walls, viable transformed L-forms formed by this technique are nevertheless useful for the anaerobic preparation of biological products and may even be preferred over organisms with regenerated cell walls for applications in which proteins produced within the cytoplasm are normally exported through the cell membrane. L-forms would offer a distinct advantage in case of purification of such proteins. Also, L-form cells of *C. perfringens,* a normally pathogenic species, have been reported to be non-pathogenic, making this organism a more suitable host for genetic engineering experiments.

Another embodiment of the present invention contemplates the creation of L-forms by the removal of the cell wall using an appropriate enzyme. Examples of the use of an enzyme to remove an anaerobic microorganism's cell wall and techniques for regenerating that cell wall are illustrated in Minton, N. P. and J. G. Morris, "Regeneration of Protoplasts of *Clostridium pasterianum* ATCC 6013," J. Bact. July 1983, pp 432–434, and in Allcoch, E. R., Reid, S. J., Jones, D. T., and Woods, D. R., "*Clostridium acetobutylicum* Protoplast Formation and Regeneration," Applied and Environmental Microbiology, Mar. 1982, pp. 719–721, which are specifically incorporated herein by reference.

Autoplasts, as stated above, are L-forms which are formed spontaneously from anaerobic microorganisms subjected to a selective environment. In the preferred embodiment of the present invention, the L-forms which are to be transformed are obtained through the use of a selective environment.

Selective environments useful for creation of autoplasts are known to those skilled in the art. Particularly preferred in the present invention are autoplasts which are created by the following method. First, the microorganisms are grown in an enriched medium containing no substance capable of acting as an osmotic stabilizer. An osmotic stabilizer, for purposes of the present invention, is a substance capable of creating an extracellular environment such that excessive swelling or shrinking of the L-forms caused by movement of water across the cellular membrane is avoided. In the most preferred embodiment of this invention, such an enriched medium which lacks an osmotic stabilizer is composed of Brain Heart Infusion (BHI) supplemented with a carbon source such as glucose.

To create autoplasts, particularly autoplasts of species of the genus Clostridium, a representative sample of the microorganisms growing in the enriched medium without the osmotic stabilizer is transferred to an enriched medium containing a high concentration of an osmotic stabilizer. In the present invention, a wide variety of sugars and salts are capable of acting as osmotic stabilizers, including, but not limited to, sugars such as sucrose and salts such as sodium chloride. In a particularly preferred embodiment of the present invention, the osmotic stabilizer is sucrose. When used as an osmotic stabilizer, sucrose is preferably present in a concentration of about 0.4 M.

The microorganisms are incubated in an appropriate anaerobic environment, in the presence of the enriched medium and the osmotic stabilizer, until wall-less cells appear, generally within 10 to 20 hours. At this point, a large percentage, generally 50% or more, of the organisms present in the medium will be autoplasts.

It is to be noted that L-forms, including autoplasts, are very fragile. In all subsequent procedures of the present invention utilizing L-forms, it is necessary to include an osmotic stabilizer in the medium. It is also necessary to perform any mechanical manipulations involving L-forms gently.

Once the L-forms are obtained, foreign genetic material capable of causing the microorganism to express a desired penotype may be introduced into the L-forms. Such an introduction of genetic material is accomplished using a technique capable of causing extracellular genetic material to pass through the cell membrane of the L-form with minimal negative effect on the viability of the L-form. Such techniques are generally known from a variety of protoplast fusion and transformation techniques known to the art. Techniques appropriate for the transformation of viable anaerobic L-forms in accordance with the present invention can be selected or modified by those skilled in the art for use in the present invention without undue experimentation in light of the teachings contained herein and the insights to be gained from them. Preferably, uptake of foreign genetic material is accomplished by mixing the extracellular genetic material and the L-forms together in a buffer containing an osmotic stabilizer and a substance capable of causing the extracellular genetic material to pass through the cell membrane of the L-forms. Preferably, the substance capable of causing the extracellular genetic material to pass through the cell membrane is a surfactant, such as is polyethylene glycol (PEG) or the like. This step is commonly referred to as the transformation step.

During the transformation procedure with wall-less cells derived by any technique, it is preferred that the cells and the foreign genetic material be maintained in a buffer containing, sucrose 0.5M, MgCl$_2$ 0.02M and maleate 0.02M (SMM). In the preferred embodiment of the present invention, the wall-less cells and plasmid DNA are mixed in this buffer, three volumes of 40% PEG in SMM (approximately 1.5 ml) are added and the mixture is held at room temperature for approximately three minutes. After this incubation period, 20–30 ml of BHI containing 0.4M sucrose medium is added to dilute the PEG, and the wall-less cells are pelleted by centrifugation. At this point, the transformation mixture may be resuspended in a small volume (0.5–1.0 ml) of BHI containing 0.4 M sucrose and plated directly upon a selective medium if the plasmid DNA used is homologous, i.e., derived from the transformed organism, preferably *C. perfringens.* If the transforming DNA is heterologous, i.e., derived from *E. coli* and transformed into *C. perfringens,* then a grow-out period of approximately 16 hours in BHI containing 0.4 M sucrose medium is conducted prior to plating on selective media for transformed cells. The desirability of this additional grow-out step is presumably due to a smaller frequency of stable transformation obtained with heterologous DNA.

The enriched, solidified medium used for plating the transformants includes an agent capable of identifying those microorganisms which were successfully transformed. In this regard, it is preferred that a portion of the foreign genetic material introduced into the L-forms confer upon them at least one selectable phenotypical trait, such as a specific antibiotic resistance. For example, if the genetic material introduced into the L-forms was capable of directing the microorganism to exhibit, as a portion of its phenotype, tetracycline resistance, then tetracycline would be included in the enriched, solidified medium. The inclusion of tetracycline in the solidified, enriched medium would prevent any L-forms that had not been transformed from growing and reproducing.

In the case of a transformation using autoplasts of *C. perfringens* as recipients, once the transformation step has been completed, the transformed L-forms are spread on a plate of solidified, enriched medium overlaid with a support surface upon which the microorganisms may grow using nutrients from the underlying medium. It is preferred that the enriched medium used in this portion of the method of the present invention contain the same nutrients as that used to obtain the autoplasts. For this portion of the present invention, the enriched selective medium described above is solidified by the addition of a solidifying agent, preferably agar. If agar is the solidifing agent, it is preferably present in a concentration of about 2%. The preferred support surface used in this step of the present invention is a filter or other porous, nonnutritive material, most preferably a nitrocellulose filter.

Transformants are allowed to grow on the support surface. If transformants are microscopically examined at this time, it will be noted that the transformants are still in a wall-less state. The transformants, still in the form of L-forms, must then be removed from the solid support and placed in contact with an enriched medium that provides an environment conducive to the re-structuring and regeneration of the cell wall. It is believed that a semi-solid medium, for example, immobilizes both the organisms and the cell wall precursors as they are excreted from the organism, thereby creating conditions favorable to assembly of a cell wall. While solid surfaces, such as solid agar surfaces, capable of providing such conditions are contemplated as being useful for this purpose, it is preferred to employ a semi-solid medium such as that created by addition to a liquid medium of solidifying agents such as gelatin or the like. When gelatin is used as an agent to create the semi-solid medium, gelatin is used in a concentration of about 10 to about 30%, preferably about 20 to about 25%, and is most preferably used in a concentration of about 25%. When single colonies derived from transformed cells are picked and inoculated into such a medium, cultures of walled transformed cells arise within 24-48 hours in virtually all cases, which cells can be shown to be harboring the transforming vector.

Vectors

When using the method of the present invention, it is preferred to transform the anaerobic microorganisms using genetic material which is capable of introduction into and expression in more than one genera of microorganism. To accomplish this objective, plasmid vectors and shuttle vectors have been invented. Plasmid vectors, as used hereinafter, are defined as plasmid molecules containing genes capable of expressing at least one phenotypical property. A shuttle vector, as used hereinafter in this application, is defined as a plasmid vector into which DNA segments may be inserted to allow the transfer of these segments into different microorganisms in which the plasmid molecule can be propagated. Shuttle vectors are capable of being introduced into microorganisms of more than one genus.

Figure 1:
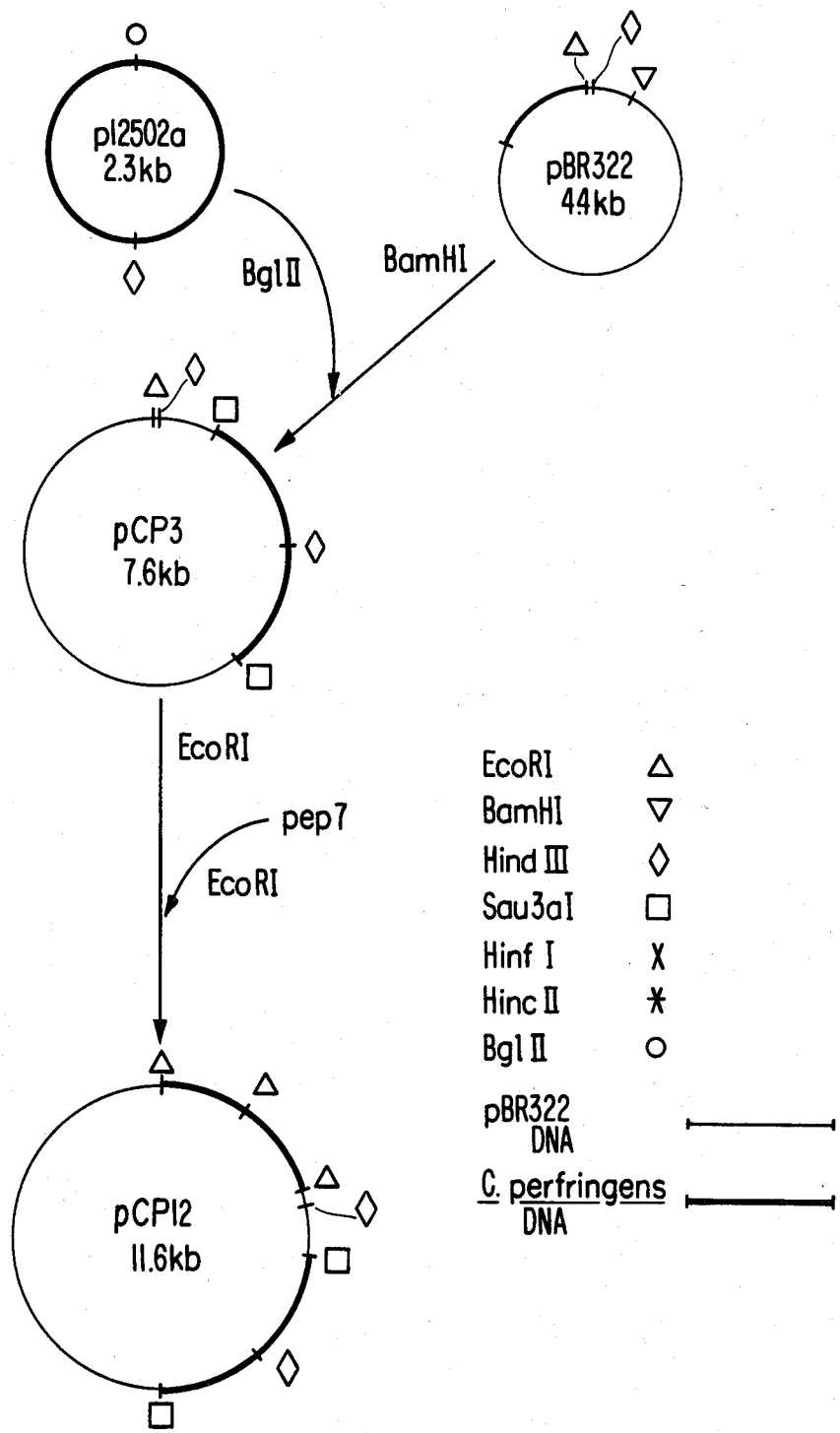
FIG. 1 illustrates the genealogy and the restriction maps of the following plasmids:
  Plasmid pCP3, which is a chimeric plasmid comprised of *E. coli* plasmid pBR322 and *C. perfringens* plasmid p12502a and which serves as a precursor for shuttle vector pCP12.
  Plasmid pCP12, which is a shuttle vector used in the transformation of *E. coli* and Clostridium perfringens.
Figure 2:
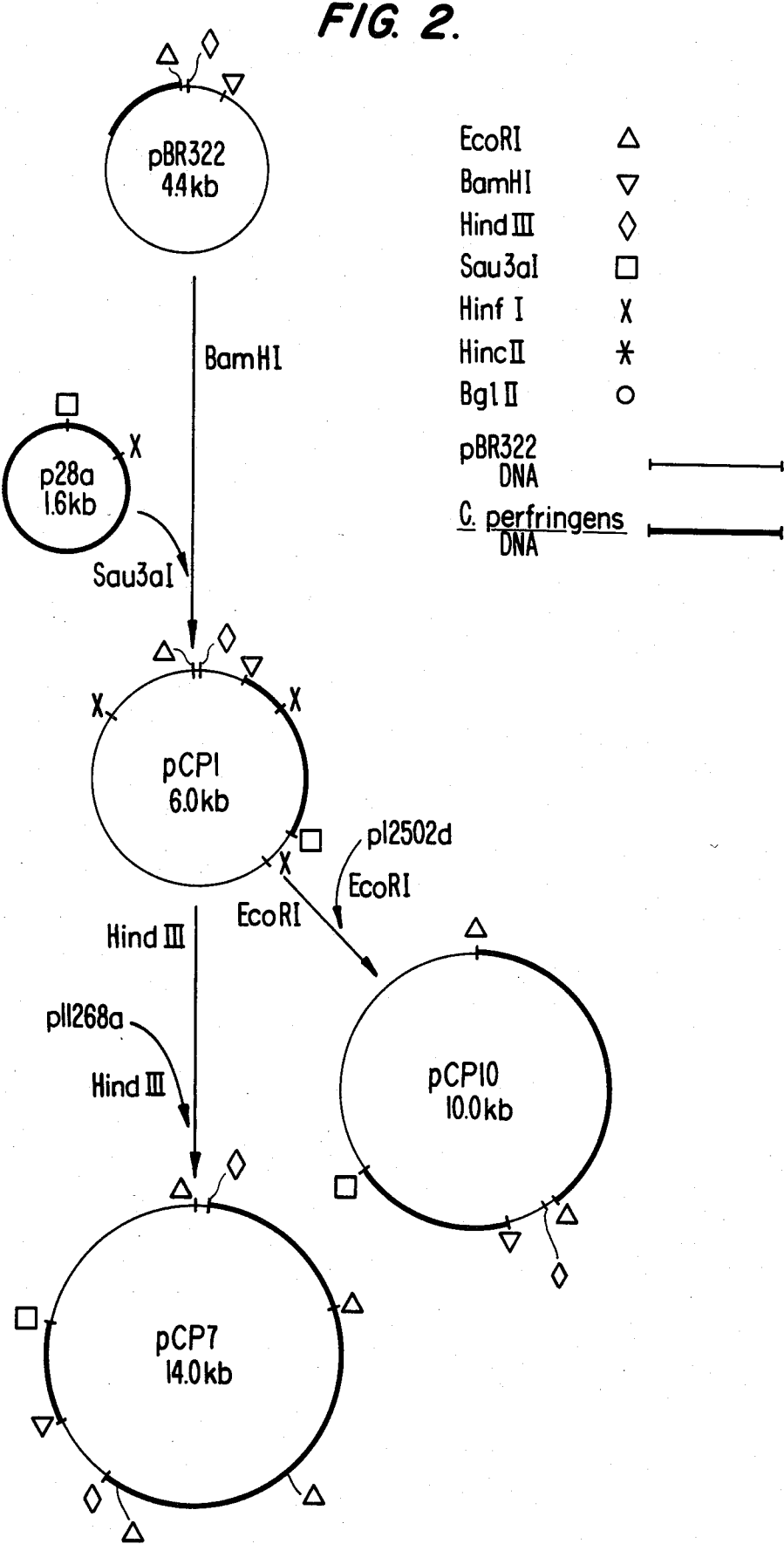
FIG. 2 illustrates the genealogy and the restriction maps of the following plasmids.

Shuttle vectors preferred for use in the transformation of anaerobic microorganisms must be capable of replicating in all microorganisms into which they are to be inserted. To accomplish this, it is necessary to insert, into each shuttle vector, a sequence of DNA capable of directing the host organism to reproduce the genetic material which constitutes the plasmid. Such a DNA sequence is referred to as an origin of replication. In the preferred embodiment of the present invention, shuttle vectors that may be transformed into both bacteria of the genus *Escherichia* and of the genus *Clostridium* have been created. These shuttle vectors contain origins of replication recognized by bacteria of both genera. The shuttle vectors of the present invention will hereinafter be referred to as pCP12, pCP13, and pCP16. The shuttle vectors may be made by the procedures and from the materials described below. The genealogy of the specific shuttle vectors described below are illustrated in FIGS. 1–3.

*Clostridium perfringens* strain 12502 plasmids

Four plasmids have been isolated from *Clostridium perfringens* strain 12502, obtainable from the Virginia Polytechnic Institute's Anaerobe Laboratory Strain Collection. These plasmids are hereinafter referred to as p12502a, p12502b, p12502c, and p12502d. Plasmid p12502d confers tetracycline resistance on this strain. These plasmids range in size from approximately 4,000–55,000 base pairs (bp). The two smaller of the four plasmids may be isolated from a mixture containing them by separation on an agarose gel. In the preferred embodiment of the present invention, the mixture of plasmids is resolved by electrophoresis in a 0.8% agarose gel containing tris-borate EDTA buffer. Agarose blocks containing the individual plasmids are then excised from the gel and passed through an 18 gauge needle. The agarose is then freeze-thawed twice, suspended in a Tris-EDTA buffer, and extracted twice with a phenol solution saturated with Tris-EDTA buffer. Following ether extraction to remove residual phenol, the solution is made 0.3M in sodium acetate and the DNA precipitated with three volumes of absolute ethanol.

p28a

*Clostridium perfringens* strain 28, obtainable from D. E. Mahoney, Dept. of Microbiology, Faculty of Medicine, Dalhousie University, Halifax, N.S. Canada B3H 4H7, contains four cryptic plasmids. The smallest of these four plasmids will hereinafter be referred to as p28a. This plasmid is obtainable by seParation from a mixture of the four plasmids found in *Clostridium perfringens* strain 28 on agarose gel.

pCP1

To create plasmid vector pCP1, as illustrated in FIG. 2, p28a was digested with Sau3aI. Endonuclease Sau3aI caused p28a to cleave at one site. One plasmid digestion fragment was therefore obtained. This digestion fragment was ligated with a digestion fragment which had been obtained by digestion of *E. coli* plasmid pBR322, obtainable from Bethesda Research Laboratories, with BamHI. Although digestion of pBR322 with BamHI destroyed the tetracycline resistance ($Tet^r$) gene native to pBR322, pCP1can direct production of the enzyme Beta-lactamase, conferring ampicillin resistance ($Amp^R$), in *E. coli.* The plasmid vector pCP1 may be isolated by techniques known to the art, see, e.g., "Advanced Bacterial Genetics," R. W. Davis, D. Botstein and J. R. Roth, Cold Spring Harbor Laboratory, Cold Spring Harbor, N.Y., which is specifically incorporated herein by reference, from the *E. coli* culture 39435 deposited in the American Type Culture Collection, Rockville, Maryland (hereinafter "ATCC").

pCP3

To create plasmid vector pCP3, as illustrated in FIG. 1, p12502a was digested with BglII. One digestion fragment was obtained and was ligated with pBR322 which had been digested with BamHI. This plasmid vector also can direct production of the enzyme Beta-lactamase, capable of conferring ampicillin resistance to *E. coli* but, like pCP*1*, cannot confer tetracycline resistance to a transformant because the $Tet^r$ gene originally present in pBR322 was destroyed during digestion with BamHI. The plasmid vector pCP3 may be isolated by above described techniques known to the art from the *E. coli* culture 39436 deposited in the ATCC.

pCP5

Plasmid vector pCP5, as illustrated in FIG. 3, was created by ligating p12502b, after digestion with BglII, with pBR322, digested with BamHI. Like pCP1 and pCP3, pCP5 can direct production of the enzyme Beta-lactamase, capable of conferring ampicillin resistance to *E. coli. The plasmid vector pCP*5 may be isolated by above described techniques known to the art from the *E. coli* cultures 39437 deposited in the ATCC.

pCP7

Plasmid vector pCP7, as illustrated in FIG. 2, was created to add to pCP1 a phenotype that could be selected for in L-forms of *Clostridium perfringens.* The beta-lactamase activity conferring ampicillin resistance on strains of *E. coli* transformed with the plasmids already discussed would be useless in the selection of transformed L-forms because the action of this drug is to prevent cell wall biosynthesis, thereby stopping cell growth. To form pCP7, pCP1 was digested with HindIII, an endonuclease which cleaves pCP1 in only one site, at an area of DNA originally from pBR322, therefore not disrupting the Clostridial origin of replication contained in the DNA originally from p28a. Fourteen or fifteen fragments of DNA, obtained from a HindIII digestion of p11268a, a single large plasmid which confers tetracycline resistance found in *Clostridium perfringens* strain 11268, obtainable from Virginia Polytechnic Institute, were combined randomly with the pCP1 fragment. The recombinant plasmids obtained from this ligation were transformed into *E. coli* and selection was made for tetracycline resistant clones. A Tet$^r$ transformant was saved and found to contain a plasmid since named pCP7. Plasmid pCP7 enables *E. coli* to produce a gene product conferring tetracycline resistance. However, pCP7 has not been shown to transform *C. perfringens*. The plasmid vector pCP7 may be isolated by above described techniques known to the art from the *E. coli* culture 39438 deposited in the ATCC.

pCP10

Plasmid pCP10, illustrated in FIG. 2, was created by digesting pCP1 with EcoRI, an endonuclease which cleaves pCP1 at one site. Into this cleavage site, DNA fragments obtained from EcoRI digestion of all four *C. perfringens* strain 12502 plasmids, p12502a, p12502b, p12502c and p12502d, were randomly ligated. A mixture of all four plasmids was used because of the difficulty of purifying p12502d which is harboring the tet gene. The recombinant plasmids obtained from this ligation were transformed into *E. coli* and selection was made for tetracycline resistant clones. One Tet$^r$ transformant was saved and found to contain a plasmid, since named pCP10. The plasmid vector pCP10 may be isolated by above described techniques known to the art from the *E. coli* culture 39439 deposited in the ATCC.

pCP12

Plasmid pCP12, illustrated in FIG. 1, capable of transforming both *E. coli* and *C. perfringens* and of being stably maintained in each, was created by digesting pCP3 with EcoRI. Into this cleavage site, the fragments obtained from an EcoRI digestion of pCP7 are ligated. Plasmid pCP12 contains two pCP7 fragments, each about 2000 bp, which presumptively confer the ability to produce the gene product conferring tetracycline resistance to *Clostridium perfringens* or *E. coli* transformants containing pCP12. The plasmid vector pCP12 may be isolated by above described techniques known to the art from the *C. perfringens* culture 39440 deposited in the ATTC.

pCP13

Plasmid pCP13, illustrated in FIG. 3, is capable of transforming both *E. coli* and *C. perfringens* and of being stably maintained in each. Plasmid pCP13 is created by digesting pCP5 with EcoRI and ligating the one fragment obtained with the multiple fragments obtained from an EcoRI digestion of pCP7. Plasmid pCP13 contains the same two pCP7 fragments as does pCP12, and they are in the same orientation with respect to one another. Presumptively, these two fragments, each about 2000 bp, confer the ability to produce the gene product conferring tetracycline resistance to *Clostridium perfringens* or *E. coli* transformants containing pCP13. The plasmid vector pCP13 may be isolated by above described techniques known in the art from the *C. perfringens* culture 39441 deposited in the ATCC.

pCP16

Plasmid pCP16, illustrated in FIG. 3, is also capable of transforming both *E. coli* and *C. perfringens* and of being stably maintained in each. Plasmid pCP16 is created by ligating the one fragment obtained by an EcoRI digestion of pCP5 with the two fragments obtained from an EcoRI digestion of pCP10. Plasmid pCP16 enables a host organism to produce the gene product conferring tetracycline resistance. The plasmid vector pCP16 may be isolated by above described techniques known in the art from the *C. perfringens* culture 39442 deposited in the ATCC.

Plasmids pCP12, pCP13, and pCP16 each contain unique restriction endonuclease digestion sites which do not lie within either origin of replication or antibiotic resistance coding sequences contained in them. A DNA sequence encoding for a desired biological product may then be ligated into any one of the shuttle vectors and may be subsequently transformed into and expressed in *E. coli* or Clostridium.

The following examples are designed to elucidate the teachings of the present invention, and in no way limit the scope of the invention. Other modifications and equivalents of the examples will readily suggest themselves to those of ordinary skill in the art, particularly after issuance of this patent, without departing from the spirit or scope of the present invention.

EXAMPLE 1—Transformation of Clostridium perfringens

The strain of *C. perfringens* (11268 CDR, ATCC 34943) used as the recipient in all transformation experiments described below is a tetracycline-sensitive (Tet$^s$) derivative of strain 11268 obtainable from the Virginia Polytechnic Institute's Anaerobe Laboratory Strain Collection. This derivative contains no plasmid.

This strain can be routinely grown in a rich medium containing Brain Heart Infusion (BHI, obtainable from Difco), prepared as described in "Anaerobe Laboratory Manual", 4th ed., L. V. Holdeman et al. eds. VPI Anaerobe Laboratory, Blacksburg, VA (1977), with 1% glucose as a carbon source. L-variants of this strain can be induced to form by its growth in petri plates containing an enriched medium of BHI, sucrose (as an osmotic stabilizer), horse serum, bovine serum albumin, and penicillin. In this preferred enriched medium, sucrose is preferably present in a concentration of about 0.4 M. Horse serum is preferably present at a concentration of about 5%. Bovine serum albumin is preferably present at about 0.5 to about 1.5%, and most preferably present at a concentration of about 0.8%, and penicillin G at about 15 µg/ml. The serum present in the enriched transformation medium, in addition to serving as an additional osmotic stabilizer, increases the nutrient content of the medium. When plated on this medium, individual walled cells of strain 11268 CDR (ATCC 39443) quantitatively give rise to colonies of wall-less (L-form) cells. If these L-form colonies are individually picked and transferred to a medium containing BHI and 0.4 M sucrose, as an osmotic stabilizer, L-forms will grow after a lag of 2–3 days to yield a turbid culture whether or not Penicillin G is present. Subsequent subculture of the L-forms into the same medium (without Penicillin G) results in growth without a lag with a doubling time of approximately 40 minutes. L-forms subjected to prolonged liquid culture as described here seem to sustain substantial impairment of their ability to synthesize a cell wall. Fresh (overnight cultures) of L-forms grown as described above may be harvested by centrifugation and used as recipients in transformation experiments to be described below.

Alternatively, wall-less cells of *C. perfringens* strain 11268 CDR (ATCC 39443) may be prepared in the following way. Walled cells of this strain are cultured in BHI+1% glucose medium at 37° C. until late in the logarithmic phase of growth. An inoculum (ten-fold final dilution) is then transferred to BHI+0.4 M sucrose medium. This culture is then allowed to incubate for 10–16 hours at room temperature. At the end of this period, the culture contains approximately 50% wall-less cells as judged by microscopic examination. These "autoplast" cells have not had their ability to regenerate a cell wall impaired if handled as described below and, after harvesting by centrifugation, may be used as recipients in transformation experiments.

Wall-less cells of *C. perfringens* strain 11268 CDR (ATCC 39443) prepared by either of the procedures described above are handled identically through the transformation procedure. Approximately 50 ml of cells are chilled on ice, transferred anaerobically to air-tight centrifuge tubes, and pelleted at 5000 rpm (Beckman JA-20). All of the following procedures are done at room temperature in an anaerobic glove box. The cells are resuspended in 0.5 ml of SMM buffer, and approximately 1 μg of plasmid DNA (described in Example 2) is added to the tube followed immediately with 1.5 ml of polyethylene glycol (M.W. approximately 8000) in SMM buffer. The mixture is allowed to stand three minutes and then 20–30 ml of BHI+0.4 M sucrose is added. The cells are repelleted and resuspended in 0.5 ml of BHI+0.4 M sucrose. At this point, depending upon whether homologous (*C. perfringens* derived) or heterologous (*E. coli*-derived) plasmid DNA was used or if stable L-forms or autoplasts were the recipient, different procedures are followed.

Stable L-forms transformed with homologous plasmid DNA may be plated directly upon petri plates containing the preferred enriched medium described above and 2 μg/ml tetracycline to select for recombinant clones (see Table 1 for typical transformation frequencies). Stable L-forms transformed with heterologous DNA are resuspended in BHI+0.4M sucrose and grown at 37° C. for 12–16 hours before selective plating as above. Inclusion of 0.02 μg/ml tetracycline in this grow-out will enrich for transformants. The desirability of this grow-out step presumably arises from the lower frequencies of transformation obtained with heterologous DNA (see Table 1).

Autoplasts transformed with homologous or heterologous plasmid DNA's must be handled accordingly as described above. In addition, since the utility of these cells arises from their ability to regenerate a cell wall, they are treated further in order to achieve this goal. An autoplast transformation mixture (either obtained directly or after grow out) is spread on a petri plate containing the preferred enriched medium supplemented with 2 μg/ml tetracycline that has been overlaid with a 0.45 μm Millipore nitrocellulose filter. After 18 hours, $Tet^r$ transformant clones arise on the filter. These clones contain all wall-less cells. If a colony is picked and transferred to medium containing BHI+0.4 M sucrose+25% gelatin, a culture of walled cells arises.

These can be shown to be harboring the transforming plasmid DNA.

TABLE 1

Transformation of L-forms of *C. perfringens* with Chimeric DNA's

| Plasmid | Source | Recipient | Frequency (Transformants/viable cell/μg DNA) |
|---|---|---|---|
| pCP12 | *E. coli* | 11268 CDR | $1 \times 10^{-8}$[a] |
| pCP13 | *E. coli* | 11268 CDR | $1 \times 10^{-9}$[a] |
| pCP16 | *E. coli* | 11268 CDR | $1 \times 10^{-9}$[a] |
| pCP12 | *C. perfringens* | 11268 CDR | $1.5 \times 10^{-7}$ |
| pCP13 | *C. perfringens* | 11268 CDR | $2 \times 10^{-7}$ |
| pCP16 | *C. perfringens* | 11268 CDR | $2.5 \times 10^{-7}$ |
| p11268a | *C. perfringens* | 11268 CDR | $2.5 \times 10^{-7}$ |

[a]Frequency of transformation in these cases is calculated considering the number of generations the culture produced during its grow-out in BHI + 0.4M sucrose medium.

EXAMPLE 2—Construction of Shuttle Vectors

When attempting to develop a genetic exchange mechanisms it is extremely useful to include the potential to clone in an organism for which a great variety of genetic techniques exist. Therefore, in the course of making a transformation system for *C. perfringens*, plasmid vectors capable of stable replication and selection in this organism and in *E. coli* were prepared. Such vectors require DNA origin of replication (ori) sequences compatible with the DNA copying apparatus of both organisms and expression of genetic phenotypes selectable in both organisms.

In order to attain the first of these goals, many available strains of *C. perfringens* were examined for plasmid DNA's. In general, these preparations were made according to the method of Rood et al. (*Antimicrobial Agents and Chemother.* 13:871–880, 1978). Three small plasmids were obtained and named p28a (1600 bp), p12502a (3300 bp), and p12502b (3900 bp). Plasmid p28a was gotten from *C. perfringens* strain 28 obtainable from D. E. Mahoney, and plasmids p12502a and p12502b were gotten from *C. perfringens* strains 12502 obtainable from the Virginia Polytechnic Institute's Anaerobe Lab Strain Collection. Both of these organisms contain four plasmids each. In order to isolate the plasmids for restriction studies and cloning, they were resolved by electrophoresis in a 0.8% agarose gel. Agarose blocks containing the individual plasmids are then excised from the gel and passed through an 18 gauge needle. The agarose was then freeze-thawed twice, suspended in a Tris-EDTA buffer, and extracted twice with a phenol solution saturated with Tris-EDTA buffer. Following ether extraction to remove residual phenol, the solution was made 0.3M in sodium acetate and the DNA precipitated with three volumes of absolute ethanol.

Each of these plasmids was found to contain a unique restriction endonuclease cleavage site compatible with the BamHI site of *E. coli* plasmid pBR322. Digestion of these plasmids with the appropriate enzyme followed by ligation into the BamHI sites of pBR322 yielded a set of recombinant plasmids capable of replication in *E. coli* and presumably in *C. perfringens.* These plasmids are called pCP1 (p28a+pBR322), pCP3 (p12502a+pBR322), and pCP5 (p12502b+pBR322). Refer to FIGS. 1 through for details concerning construction of these plasmids.

Plasmids pCP1 pCP3, and pCP5 replicate stably in *E. coli* and confer resistance to ampicillin in this organism (the Tetr$^r$ phenotype of pBR322 having been destroyed in the cloning process). While each of these should be capable of replication in *C. perfringens* as well, no direct test of this has been conducted because the L-forms used as recipients in this transformation procedure, being wall-less, are not affected by ampicillin. Accordingly, another antibiotic resistance coding sequence from *C. perfringens* was cloned into *E. coli* on plasmids pCP1, 3, and 5, and then these new multiply marked cloning vectors were used to transform *C. perfringens.*

Two Tet$^r$ strains of *C. perfringens* 11268 and 12502 (both obtainable from the Virginia Polytechnic Institute's Anaerobe Laboratory Strain Collection) contain similar large (55 kb) plasmids that we had shown to harbor coding sequences for tetracycline resistance. These plasmids are named p11268a and p12502d. These sequences were cloned to plasmid pCP1 followed by transformation of *E. coli* strain HB101 with selection for Tet$^r$ clones at the minimum inhibitory concentration of tetracycline for this strain, 4 $\mu$g/ml. Accordingly, plasmid p11268a was digested with restriction endonuclease HindIII (generating approximately 15 fragments) and these were ligated to plasmid pCP1 cut with the same enzyme. Also, plasmid p12502d was digested with restriction endonuclease EcoRI (generating 9 fragments) and these were ligated to plasmid pCP1 digested with the same enzyme. Tet$^r$ clones arose following transformation of *E. coli,* specifically *E. coli* strain HB101 as described in the Davis reference supra, with the mixtures of recombinant DNA's described above. From each experiment, a single Tet$^r$ clone was saved and characterized. These were found to be harboring recombinant plasmid DNA's that were called pCP7 (pCP 1 +p11268a) and pCP10 (pCP1+p12502d). Refer to FIGS. 1 through for details on construction of these plasmids.

Plasmid pCP7 has an approximately 8 kb DNA insert derived from p11268a containing several HindIII sites. Plasmid pCP10 contains a 4 kb EcoRI fragment derived from plasmid p12502d. These DNA inserts contain some homologous DNA sequences (as determined by DNA-DNA hybridization) pointing to the similarity of the cloned tet genes.

From plasmids pCP7 and pCP10, the tet genes were subcloned to pCP3and pCP5 using enzyme EcoRI in both cases to yield plasmids pCP12, pCP13, and pCP16 (see FIGS. 1 through 3). All of these are both topographically and temporally stable in *E. coli.* High curing rates or rearrangements due to recombination have never been observed.

Plasmids pCP12, pCP13, and pCP16 have been used in successful transformation experiments with L-forms and autoplasts of *C. perfringens* strain 11268 CDR (ATCC 39443) as described in Example 1.

It will be apparent to those skilled in the art that various modifications and variations can be made in the methods of the present invention without departing from the scope or spirit of the invention. Thus, it is intended that the present invention cover the modifications and variations of the invention provided they come within the scope of the appended claims.

What is claimed is:

1. The plasmid vector pCP1.

2. The plasmid vector pCP3.

3. The plasmid vector pCP5.

4. The plasmid vector pCP7.

5. The plasmid vector pCP10.

6. The shuttle vector pCP12.

7. The shuttle vector pCP13.

8. The shuttle vector pCP16.

* * * * *